United States Patent [19]

Jones et al.

[11] Patent Number: 4,925,102
[45] Date of Patent: May 15, 1990

[54] KITCHEN AND BATH USES

[76] Inventors: Christine B. Jones, Rte. 4, Box 355, Gate City, Va. 24251; George Spector, 233 Broadway, Rm. 3815, New York, N.Y. 10007

[21] Appl. No.: 248,119

[22] Filed: Sep. 23, 1988

[51] Int. Cl.$^5$ .............................. A61L 9/04
[52] U.S. Cl. ........................ 239/52; 108/27; 239/57; 239/273; 239/289; 242/55.55; 312/277; D6/523; D6/536
[58] Field of Search .............. 239/34, 52, 57, 273, 239/282, 283, 289; 242/55.55; 312/277; 108/27, 90; D6/523, 524, 536; 248/309.1

[56] References Cited

U.S. PATENT DOCUMENTS

| D. 239,347 | 3/1976 | Vrignaud | D6/523 |
| 1,644,503 | 10/1927 | Aumack | 239/57 |
| 1,794,016 | 2/1931 | Henry | 239/52 |
| 3,017,117 | 1/1962 | Klingler | 239/52 |
| 3,329,367 | 7/1967 | Paradiso | 242/55.55 |
| 3,558,055 | 1/1971 | Storchheim | 239/34 |
| 3,848,822 | 11/1974 | Boone | 239/52 |
| 3,943,859 | 3/1976 | Boone | 108/27 |
| 4,154,398 | 5/1979 | Gualandi | 239/59 |

Primary Examiner—Andres Kashnikow
Assistant Examiner—Michael J. Forman

[57] ABSTRACT

An air freshener holder is provided and consists of an elongated perforated housing for supporting consumable items therefrom and material located within the housing for giving off a fragrance to the surrounding atmosphere. The consumable items can be a toilet paper roll, a paper towel roll, a bar of soap and facial tissues.

1 Claim, 1 Drawing Sheet

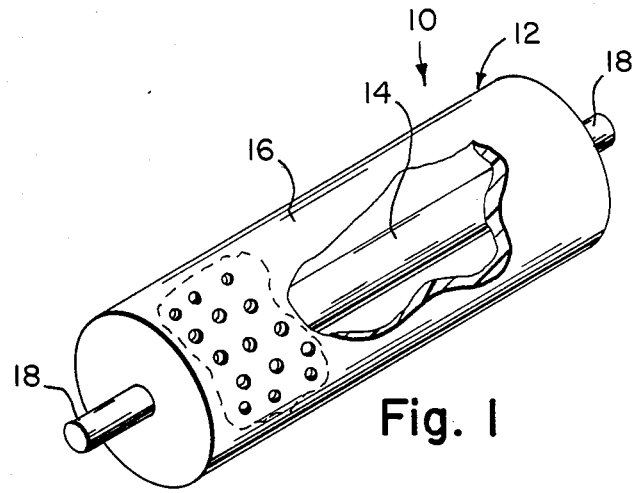
Fig. 1
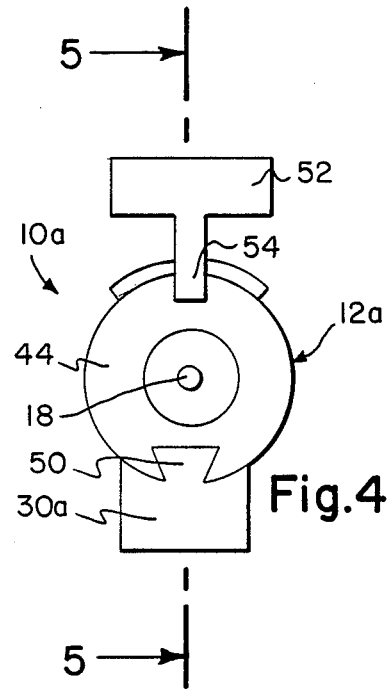
Fig. 4
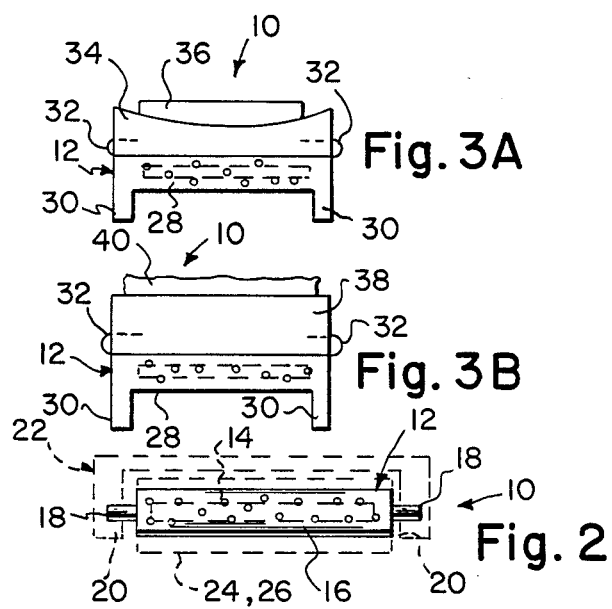
Fig. 3A
Fig. 3B
Fig. 2
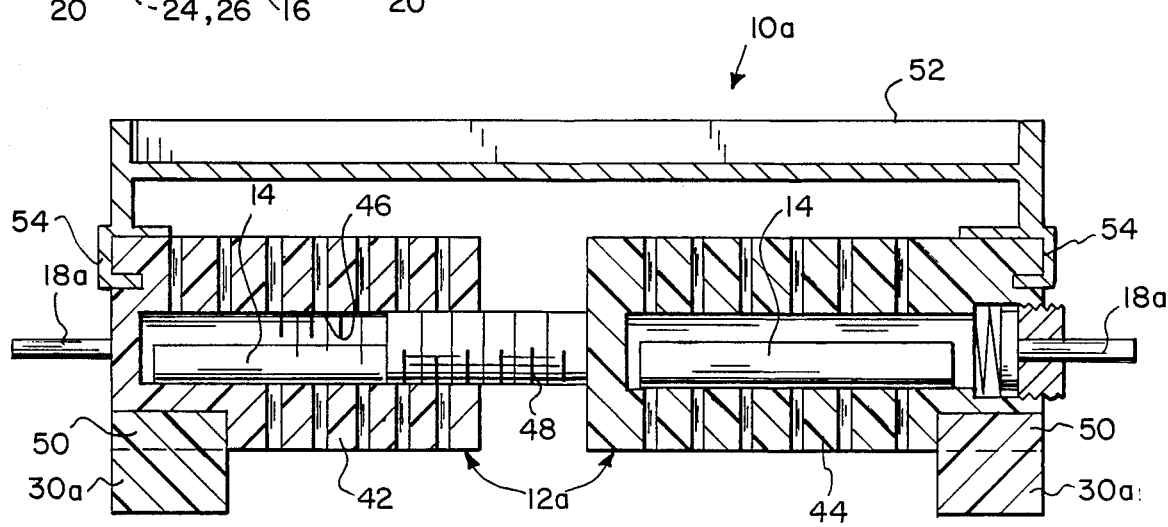
Fig. 5

KITCHEN AND BATH USES

BACKGROUND OF THE INVENTION

The instant invention relates generally to dispensing devices and more specifically it relates to an air freshener holder.

Numerous dispensing devices have been provided in prior art that are adapted to include tubular housings for holding releasable materials therefrom. For example, U.S. Pat. Nos. 1,794,016; 3,017,117 and 3,848,822 all are illustrative of such prior art. While these units may be suitable for the particular purpose to which they address, they would not be as suitable for the purposes of the present invention as heretofore described.

SUMMARY OF THE INVENTION

A primary object of the present invention is to provide an air fresener holder that will overcome the shortcomings of the prior art devices.

Another object is to provide an air freshener holder that includes a perforated housing containing material therein which gives off a fragrance to the surrounding atmosphere.

An additional object is to provide an air freshener holder that can be physically changed into a toilet paper, soap dish, tissue and paper towel holder with the fragrance material therein.

A further object is to provide an air freshener holder that is simple and easy to use.

A still further object is to provide an air freshener holder that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a perspective view of the invention with parts broken away as a toilet paper or paper towel holder.

FIG. 2 is a front view thereof.

FIG. 3A is a front view showing the invention as a soap dish holder.

FIG. 3B is a front view showing the invention as a facial tissue holder.

FIG. 4 is an end view of a modification in which the invention can be adjusted to be used as the toilet paper holder, the soap dish holder, the facial tissue holder and paper towel holder.

FIG. 5 is a cross sectional view taken along line 5—5 in FIG. 4 showing the structures for adjusting the invention.

DETAILED DESCRIPTION OF THE PREFERRED EMBODIMENTS

Turning now descriptively to the drawings, in which similar reference characters denote similar elements throughout the several views, FIGS. 1 and 2 illustrate an air freshener holder 10 which consists of an elongated perforated housing 12 for supporting consumable items therefrom. Material 14 located within the housing 12 is for giving off a fragrance to the surrounding atmosphere. The perforated housing 12 is in the form of a tubular roller 16 having opposite stub axles 18 that can be journalled in sockets 20 of a wall mounted bracket 22 shown in phantom in FIG. 2. In one instance the perforated housing 12 can be sized for a toilet paper roll 24 and in another instance the perforated housing 12 can be sized for a paper towel roll 26 to be suspended therefrom.

FIGS. 3A and 3B show the perforated housing 12 in the form of a rectangular box-like body 28 having opposite legs 30 extending downwardly therefrom and opposite hooks 32 extending upwardly therefrom. In FIG. 3A a soap dish 34 can be attached to the hooks 32 allowing a bar of soap 36 to be contained thereon to be used therefrom. In FIG. 3B a facial tissue box 38 can be attached to the hooks 32 allowing facial tissues 40 to be dispensed therefrom.

FIGS. 4 and 5 shows a modified air freshener holder 10a wherein the perforated housing 12a is divided into two segments 42 and 44. One segment 42 has an internal threaded bore 46 while other segment 44 has an external threaded shaft 48 threadable into the bore 46 so that the perforated housing 12a can be adjustable into various longitudinal lengths.

A pair of legs 30a are each removably mounted below one of the stub axles 18a of the perforated housing 12a by a dove tail connection 50 thereto. A tray 52 is removably mounted above the stub axles 18a of the perforated housing 12a by a clamp connection 54 thereto. In one instance a bar of soap (not shown) can be contained in the tray 52 to be used therefrom and in another instance a facial tissue box (not shown) can be contained in the tray 52 allowing facial tissues to be dispensed therefrom.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An air freshener holder which comprises:
   (a) an elongated perforated housing for supporting consumable items therefrom; and
   (b) material located within a central chamber in said housing for giving off a fragrance to the surrounding atmosphere; wherein said perforated housing is in the form of a longitudinal tubular roller having opposite ends with stub axles that can be journalled in sockets of a wall mounted bracket so that in one instance a toilet paper roll and in another instance a paper towel roll can be suspended therefrom and wherein said housing has transverse perforations which communicate with said chamber, wherein said perforated housing is divided into two segments, in which one of said segments having an internal threaded bore while the other of said segments having an external threaded shaft threadable into said bore so that said perforated housing can be adjustable into various longitudinal lengths to accommodate said toilet paper roll or paper towel roll, further comprising:
   (c) a pair of legs each removably mounted on one of said segments below one of said stub axles of said perforated housing by a dove tail connection thereto; and (d) a tray removably mounted on said perforated housing above said stub axles of said perforated housing by a clamp connection whereby said holder can be converted from an air freshener paper roll holder supported on said axles to a combined air freshener holder and tray supported on legs.

* * * * *